(12) United States Patent
McKay

(10) Patent No.: US 7,923,432 B2
(45) Date of Patent: Apr. 12, 2011

(54) IMPLANT DEPOTS TO DELIVER GROWTH FACTORS TO TREAT AVASCULAR NECROSIS

(75) Inventor: William F. McKay, Memphis, TN (US)

(73) Assignee: Warsaw Orthopedic, Inc.

( * ) Notice: Subject to any disclaimer, the term of this patent is extended or adjusted under 35 U.S.C. 154(b) by 702 days.

(21) Appl. No.: 11/595,087

(22) Filed: Nov. 9, 2006

(65) Prior Publication Data

US 2007/0259018 A1  Nov. 8, 2007

Related U.S. Application Data

(63) Continuation-in-part of application No. 11/418,947, filed on May 5, 2006.

(51) Int. Cl.
- A61K 38/16 (2006.01)
- A61K 38/18 (2006.01)
- A61K 38/19 (2006.01)
- A61K 38/29 (2006.01)
- A61K 38/30 (2006.01)
- A61K 38/39 (2006.01)
- A61K 38/21 (2006.01)
- A61F 2/02 (2006.01)
- A61F 2/28 (2006.01)

(52) U.S. Cl. .......... 514/16.7; 514/1.1; 514/2.3; 514/7.6; 514/8.1; 514/8.2; 514/8.5; 514/8.8; 514/8.9; 514/9.1; 514/11.8; 514/12.2; 514/17.2; 514/20.6; 514/20.9; 424/85.5; 424/130.1; 424/422; 424/423; 424/425; 424/428

(58) Field of Classification Search .......... None
See application file for complete search history.

(56) References Cited

U.S. PATENT DOCUMENTS

| | | | |
|---|---|---|---|
| 5,656,492 A * | 8/1997 | Glowacki et al. .......... 435/284.1 |
| 6,274,159 B1 | 8/2001 | Marotta et al. |
| 6,346,123 B1 | 2/2002 | McKay et al. |
| 6,371,988 B1 | 4/2002 | Pafford et al. |
| 6,613,091 B1 | 9/2003 | Zdeblick et al. |
| 6,827,720 B2 | 12/2004 | Leali |
| 2003/0135214 A1 * | 7/2003 | Fetto et al. ................ 606/72 |
| 2004/0097469 A1 * | 5/2004 | Little et al. ................ 514/89 |
| 2005/0152949 A1 | 7/2005 | Hotchkiss et al. |
| 2006/0263355 A1 * | 11/2006 | Quan et al. ................ 424/141.1 |

OTHER PUBLICATIONS

Lin et al., Oper. Tech. Orthop., 2005, vol. 14:251-258.*
Giosue et al., Am. J., Respir. Crit. Care Med., 1998, vol. 158(4):1156-1162.*

* cited by examiner

*Primary Examiner* — Elizabeth C. Kemmerer
*Assistant Examiner* — Xiaozhen Xie

(57) ABSTRACT

The present invention relates to the design and composition of a depot implant for optimal delivery of growth factors to treat bone avascular necrosis, in that such depot implant is constructed to be in a cylinder (rod) or sphere shape and have a natural or synthetic polymer scaffold with or without impregnated calcium phosphate particles. The density of the depot is higher than a typical BMP sponge carrier to facilitate its implantation and slower release of the growth factor. The scaffold is such that it has adequate porosity and pore size to facilitate growth factor seeding and diffusion throughout the whole of the bone structure resulting in increased new blood vessel growth and density in the avascular necrotic bone. In addition, the shape of the depot implant allows for delivery through a cannula or large bore needle.

14 Claims, 4 Drawing Sheets

IMPLANT DEPOTS TO DELIVER GROWTH FACTORS TO TREAT AVASCULAR NECROSIS

CROSS-REFERENCE TO RELATED APPLICATIONS

This application is a continuation-in-part and also claims priority from U.S. application Ser. No. 11/418,947, filed on May 5, 2006 and incorporated herein by reference.

FIELD OF THE INVENTION

The present invention relates to the design and composition of an implant that is used as a growth factor depot to treat avascular necrosis (AVN). More particularly, the depot is in the shape of a small cylinder (straight or curved) or sphere that can be delivered into avascular necrotic bone through a cannula or large bore needle.

BACKGROUND OF THE INVENTION

Fractures of the proximal femur are devastating events for individuals, particularly for the elderly for whom these type of injuries are frequent. In the United States alone there are more than 300,000 (Hudson et al. Clin Orthop: pp. 59-66, 1998) hip fractures and by the year 2050 the number is expected to double (Koval and Zuckerman, J. Am Acad Orthop Surg: 2(3) pp. 141-149, 1994; Montgomery and Lawson: Clin Orthop: pp. 62-68, 1978). AVN, also known as osteonecrosis, aseptic necrosis, ischemic bone necrosis, or osteochondritis dissecans, is an impairment of blood flow to bone tissues resulting in the subsequent death of the bone tissue and eventual fracture. AVN most commonly occurs in individuals between the ages of 30 and 60. Although it can occur in any bone, AVN most commonly affects the ends of long bones or the epiphysis, such as the femur. Other common sites are the humerus, knees, shoulders, and ankles. The disease can affect one or more bones at the same time or at different times. AVN can also be involved in other bones diseases, such as osteoarthritis.

Avascular necrosis of the bone or osteonecrosis has several causes. The loss of blood supply to the bone can be caused by traumatic or non-traumatic injuries, or increased pressure within the bone that causes the blood vessels to narrow and thus decreasing blood flow to bone tissues. During traumatic injuries, such as fractures or dislocations, the blood vessels can be damaged leading to comprised blood flow. This type of AVN may develop in more than 20% of the people with dislocated hip joints. The most common post-traumatic AVN are the femoral and humeral heads, the body of the talus, and the carpal scaphoid. Post-traumatic AVN arises because of impaired blood flow and is therefore dependent on the relative contributions of arterial blood flow to the femoral or humeral head and the extent of anastomoses for collateral blood flows.

In traumatic injuries, hip dislocations may tear the ligamentum teres and the joint capsule, hence compromising the blood vessels lying in the capsular reflections. Usually individuals with hips that remain dislocated for greater than 12 hours, 52% develop AVN. In individuals who's hip dislocations remain dislocated for less than 12 hours, usually 22% develop AVN. During postfracture fixation, the incidence of AVN ranges form 11 to 45% and does not seem to be related to the surgeon's skill or fixation device. Further, arthritic changes occurring in patients three or more years after a femoral neck fracture appear to be initiated by the collapse and fragmentation of small areas of AVN in or near the weight bearing region of the femoral head.

There are many other diseases or disorders that block the small blood vessels that supply the ends of long bones causing AVN. Non-traumatic causes include, but are not limited to, alcohol abuse, high doses of corticosteroids, especially when given for a prolonged period of time, diver's decompression sickness, sickle cell disease, Gaucher's disease, tumors, such as lymphomas, radiation therapy, and certain blood clotting disorders. However, in about 25% of people with AVN the cause is unknown. There are two major theories for the mechanism of action in the development of AVN in non-traumatic causes, intra- and extraluminal obliteration of the end blood vessels. Intraluminal obliteration can be caused for example, by fat emboli, sickle cells, or nitrogen bubbles during a diver's decompression sickness. Extraluminal obliteration can be caused for example, by increased bone marrow pressure due to Guacher cell proliferation or increased marrow fat. In addition there is also an idiopathic AVN. According to the American Academy of Orthopedic Surgeons, about 10,000 to 20,000 people develop osteonecrosis each year.

To determine the appropriate treatment for AVN the conditions must first be identified. However, in many patients AVN is often painless, at least in the beginning of the disorder. In fact, in the early stages patients may be asymptomatic and only as the disease progresses will patients experience joint pain. At first the pain emerges during weight bearing on the affected joint and later the pain remains even at rest. As AVN progresses the bone and surrounding joint surface may collapse and pain will then dramatically increase. Pain may become severe enough to limit the range of motion in the affected joint. Further involvement may also lead to debilitating osteoarthritis. In addition to a complete physical exam and medical history one or more imaging techniques may be required to diagnose AVN. X-rays and computed tomography (three dimensional x-rays) are useful to detect certain AVN conditions, such as, as the presence of bone collapse or osteoarthritis. That is, advanced stages of the disorder.

Therefore, AVN is frequently not diagnosed in its early stages and the disease may progress to advanced stages thus leading to the collapse of the joint. When traumatic injuries cause AVN, the disorder cannot be detected microscopically for days to weeks and may not be detected on x-rays for months after the injury. Magnetic resonance imaging (MRI) is the test of choice to detect or diagnose early AVN.

Appropriate treatment for AVN is essential to prevent the deterioration of the joint, pain, limitation of movement and subsequent disabilities. For most AVN conditions treatment is an ongoing process, and the goal is to improve the patient's mobility of the affected joint, stop further bone damage and ensure bone and joint survival. Conservative treatments are limited to drugs to reduce blood lipids, reducing blood clotting, use of nonsteroidal anti-inflammatory drugs (NSAIDs), reduced weight bearing, range of motion exercises, or electrical stimulation to induce bone growth. However, most AVN patients will eventually need surgery.

The simplest surgical procedure is core decompression, which involves removing the inner layer of bone of the affected region, that is, cutting out a plug of bone from the internal section of the bone to reduce the internal pressure. This permits an increase in blood flow to the area and allows blood vessel formation. This procedure appears to work best in individuals in the earliest stages of AVN, before progression to bone collapse and can reduce pain and slow progression of bone and joint destruction.

Another procedure is osteotomy, and this procedure involves reshaping the bone to reduce stress on the affected area. This practice is usually effective in individuals with advanced AVN and with a large area of affected bone. Recovery is lengthy and the patient's activities are very limited for 3 to 12 months. Another procedure is the use of bone grafting. This method can also be used after a core decompression procedure. The practice is to transplant healthy bone from another part of the patient's body to the AVN affected area. Commonly the bone grafts include vascular tissues, that is, include both artery and veins to increase and maintain blood supply to the AVN affected area. This method is complex and its effectiveness is not yet proven and the recovery period is usually 6-12 months. To be successful the body has to form not only new bone but also a new blood supply.

For people who are not good candidates for the procedures, arthroplasty or total joint replacement may be necessary. This is the only effective treatment in late stage AVN, when the joint is destroyed or when AVN has caused significant osteoarthritis on the other side of the joint. However, artificial joints do not last forever and in young people they may require replacement one or more times during the individual's lifetime. Various types of joint replacements are available, including a femoral head resurfacing process, and using a metal cap over the femoral head if the socket of the hip joint is not involved.

AVN has also been increasingly associated with the human immunodeficiency virus (HIV) disease, often with bilateral hip involvement. Whether, these individuals have the established risks factors or are at an increased risk due to the disease or its antiretroviral therapy requires further epidemiological studies.

An advantageous treatment result for a patient with AVN would be an increase blood flow to the affected area and hence new bone formation. New bone formation is accomplished by one or more mechanisms such as osteogenesis, osteoconduction and osteoinduction. However, for bone growth an adequate blood supply is required.

A system and method of treating osteonecrosis is described in U.S. Pat. No. 6,827,720 (the '720 patent). The '720 patent describes a technique of drilling channels in bone and inserting growth factors followed by a plug (not containing BMP) which compresses the growth factors. The channel is sealed with a plug or screw which is advanced into each channel and compacts the bone growth inducing compound. The bone growth compound is therefore biased toward the distal end of the channel. The compacting event forces the compound into the necrotic section of bone and the pressure causes the distal bone-voids to be filled with bone growth material. The plug or screw reinforces the subchondral bone and adds structural strength to the necrotic bone preventing collapse of the bone.

The present invention does not use a plug or screw to compact the bone growth factor implant. Further, screws are not required for structural stability, the implant is not biased toward the distal end of a channel, and tapping threads in the channel are also not required to advance a screw and compact the implant. In addition, the biological site identified for the angiogenesis implant does not require maintained structural support until new bone and vasculature develop (as described in the '720 patent). In the present invention, the implant provides angiogenesis in the identified site throughout the implant site and not just in the distal end of a channel. The entire procedure is less invasive and the implant is biocompatible and biodegradable and without the potential problem of future operations to remove screws or add additional compound in the channel left behind.

SUMMARY OF THE INVENTION

The present invention fills the foregoing need by providing angiogenesis via a growth factor depot implant and system for facilitating implantation of the depot into a host bone comprising implanting an implant depot loaded with a growth factor. Local delivery of a growth factor will result in 10-50% increase in bone mineral density within a few months. In addition to direct bone stimulation growth factors will induce angiogenesis and hence treat and alleviate the AVN bone problem.

The stimulation of angiogenesis and new bone formation a few centimeters around the growth factor depot implant may cause the target bone to survive and avoid eventual fracture or collapse. The depot implant is placed within the AVN area of the bone corresponding to the local range of growth factor release. For example, growth factors strategically positioned in the AVN area of a femoral head can cause the femoral head to survive and delay or avoid the need for a hip prosthesis.

In accordance with a first aspect of the present invention, a growth factor depot implant design provides a physical feature to facilitate implantation and retention of the implant in the desired anatomical location for optimal clinical efficiency in treating AVN.

In an embodiment of the invention, the depot implant is in the shape of a small cylinder (straight or curved rod) or sphere that can be delivered into the AVN area of the bone through a cannula or large bore needle. In a preferred embodiment, the depot would be about 1 to about 5 mm in diameter and about 5 to about 20 mm in length.

In another embodiment of the invention, provision is made for the depot implant to have a composition comprising a dense collagen scaffold impregnated with calcium phosphate particles. In yet another embodiment of the invention, the scaffold is designed with a central hollow cavity that can be filled with a growth factor. In a preferred embodiment such growth factor is then slowly released through the porous depot walls.

Another aspect of the invention provides for application of the growth factor to the depot during fabrication of the depot. A preferred embodiment of the invention provides for a method of applying the growth factor to the depot at the time of surgery comprising dripping on or soaking in a solution of growth factor and, optionally further, can be placed into the internal structure of the dense depot by placing the depot into a vacuum chamber intra-operatively. Yet further, the growth factor can be injected into the depot.

Advantages of the design and composition of the implant depot are such that a slow release of the growth factor can be maintained, thus avoiding transient bone resorption near the implant due to a high release rate or the high dose of growth factor in the depot. Another advantage to the design and composition of the implant depot is the prevention of entrance of the growth factor into the venous system.

These and other objects and advantages of the present invention will be apparent from the descriptions herein.

DEFINITIONS

Figure 1:
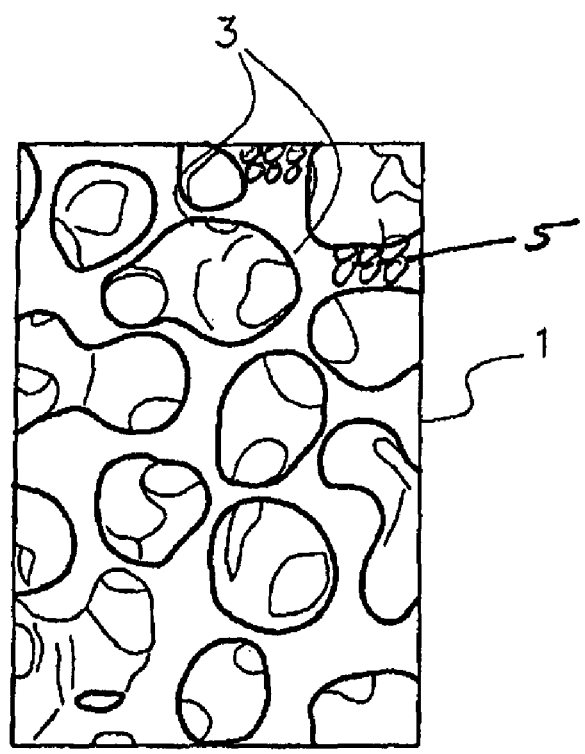
FIG. 1 depicts a relative comparison between normal bone in a healthy individual versus bone with AVN.
Figure 1:
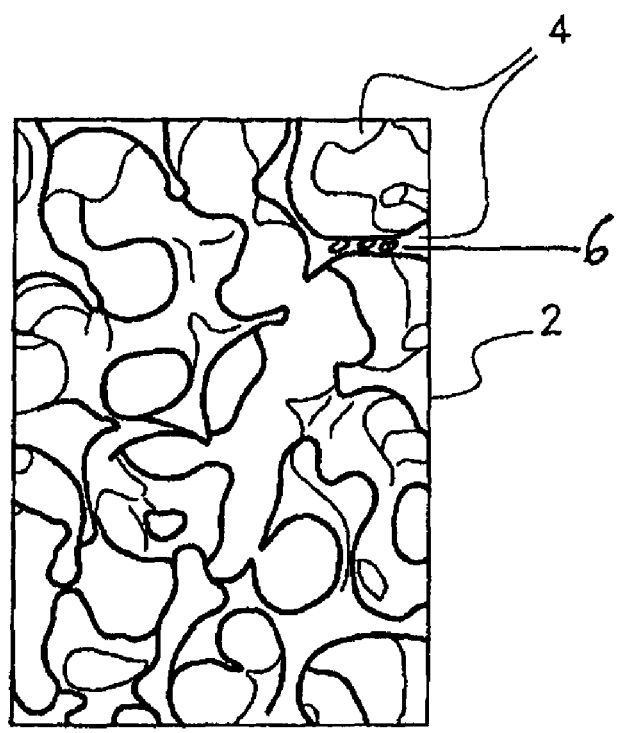

To aid in the understanding of the invention, the following non-limiting definitions are provided:

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft should ideally contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term angiogenesis refers to the stimulation and generation of the growth of new blood vessels in the AVN region of the bone.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

DETAILED DESCRIPTION

To appropriately treat AVN the disorder must first be identified. Identification is usually performed by MRI techniques to establish a visual image of the AVN area. MRI is a sensitive and specific technique used for early diagnosis of AVN and hence the region of interest can be identified and treatment can be started before collapse of the femoral head or other bone structure. Once the region of interest has been identified if invasive procedures are required then the standard surgical procedures for gaining access to the target site are used for implantation of the growth factors. If transdermal procedures are used to implant the growth factors then appropriate procedures (as described infra) are used to deliver the implant to the target sites. That is, administering the therapeutic agent to the target site for the stimulation of angiogenesis.

To improve the treatment shortcomings of AVN with the previously described procedures, an angiogenesis procedure is required. That is, increasing the blood supply to the AVN area through the stimulation of blood vessel generation with the use of growth factors. The use of growth factors implanted to the target site to generate new blood vessel growth.

For the purposes of promoting an understanding of the principles of the invention, reference to preferred embodiments and specific language will be used to describe the same. It will nevertheless be understood that no limitation of the scope of the invention is thereby intended, and that alterations and further modifications of the invention and such further applications of the principles of the invention as herein being contemplated would normally occur to one skilled in the art to which the invention relates.

Referring now to the figures, FIG. 1 illustrates a microscopic picture regional view of the condition of normal bone 1 versus that of AVN bone 2. Bone normally has an internal mesh-like structure, the density of which may vary at different points. However, AVN causes loss of bone tissue, that is, the death of the cellular elements of bone. During this process the outline of individual cells may become indistinct and the affected cells may also merge forming a granular amorphous material. This process also leads to reduced density, such that the bone micro-architecture is disrupted and the amount and variety of non-collagenous proteins in bone is changed. In other words and as can be seen from such view, the porosity of the spacing 3 of the bone tissue in a normal bone 3 is much denser than that of the porosity of the spacing 4 of the bone tissue in an AVN bone 2. The schematic view of FIG. 1 indicates schematically the normal cellular components 5 and the disrupted cellular elements 6. The spacing 6 shows that the number of cells has decreased and the outline or configuration of the cells has being altered due to cellular necrosis. Therefore the amount of bone tissue has decrease due to a lack of blood supply. Such a decrease in bone also eventually results in an increase in spacing. The AVN bone then cannot withstand normal stresses due to body weight or stresses involved during mobility and fracture or collapse of the bone occurs.

In the practice of the invention the growth factors include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268; and 6,858,431, and in Wozney, J. M., et al. (1988) *Science*, 242(4885):1528-1534. Bone morphogenic proteins have been shown to be excellent at growing bone and there are several products being tested. Extensive animal testing has already been undertaken, and human trials are finished and in process for these products. rhBMP-2 delivered on an absorbable collagen sponge (INFUSE® Bone Graft, Medtronic Sofamor Danek, Memphis, Tenn.) has been used inside titanium fusion cages and resulted in fusion in 11 out of 11 patients in a pilot study and 99% of over 250 patients in a pivotal study. In July, 2002 INFUSE® Bone Graft received FDA approval for use in certain types of spine fusion. A pilot study with BMP-2 delivered on a ceramic carrier was recently published and reported a 100% successful posterolateral fusion rate. BMP-7 (OP-1) has reported 50-70% successful posterolateral lumbar fusion results in human studies to date. On May 4, 2004, INFUSE® Bone Graft was approved for acute, open fractures of the tibial shaft (Bosse et al. *NEJM* 347(24): 1924-1931, 2002; Govender et al. *JBJS* 84(12): 2123-2134, 2002). Studies with these and other BMP's are underway. However, it is important to note that use of BMP's may add cost to an already very expensive operation. The present invention applies the same procedure and growth factors to bone with AVN. These growth factors stimulate the growth of new blood vessels to prevent further AVN and also reverse the AVN process. The treatment of AVN is a new use of these growth factor depot implants.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II), as disclosed in the U.S. Pat. No. 6,630,153, and PTH, PGE2-agonist, granulocyte colony stimulating factor (G-CSF), vascular endothelial growth factor (VEGF), matrix metalloproteinase (MMP) and statins.

Figure 2:
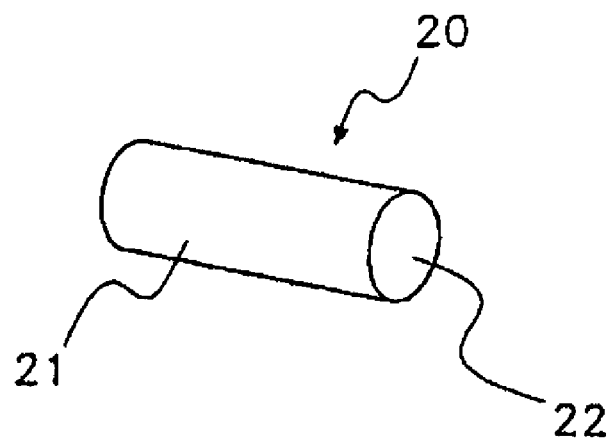
FIG. 2 depicts a perspective view of one embodiment of a growth factor depot implant.

Referring now to FIG. 2, an example of a growth factor depot implant 20 is illustrated. The depot implant 20 can either be in the shape of a small cylinder (straight or curved rod) or sphere, and in construction may be either cannulated or solid. The surface of the depot implant may be either smooth, threaded, or any combination thereof. Herein, the cylinder or rod shape is intended to indicate any shape with a longitudinal axis longer along one direction than in other directions. As shown in the longitudinal direction, the depot implant 20 is constructed such that it is usually 5 to 20 mm in length and such that its surface can be either a smooth or convoluted surface 21. The cross-sectional shape across the longitudinal axis may be any shape, but is preferably elliptical or circular. In addition, the depot implant may be either straight or curved in such longitudinal direction. As shown in vertical direction, the depot implant 20 is constructed such that it is 1 to 5 mm in diameter and such that its end surface 22 can be shaped such that it is either flat, rounded, spherical or convoluted in shape.

Figure 3:
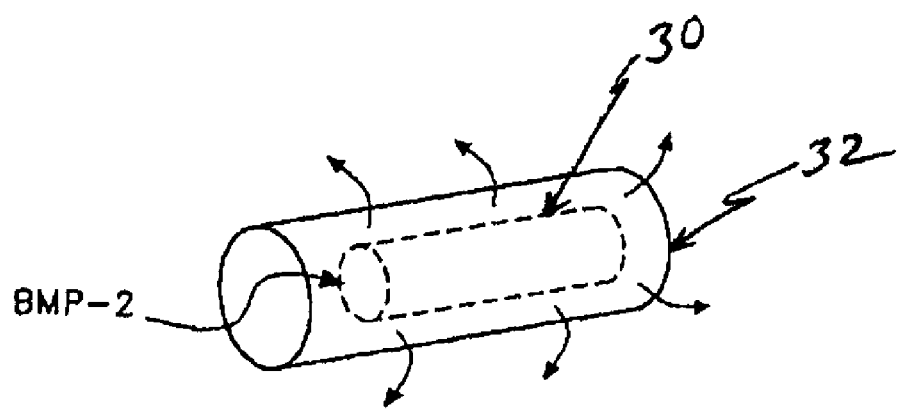
FIG. 3 depicts a perspective view of another embodiment of a growth factor depot implant.

Referring now to FIG. 3, another example of a growth factor depot implant 32 is illustrated. In this embodiment, depot implant 32 is cylindrical in shape, but is constructed such that it has a hollow interior chamber 30 (shown by the dotted line). Chamber 30 may itself follow the exterior cylindrical shape or may be of any shape, in so long as the exterior structure is not compromised. In a preferred embodiment, the chamber 30 is filled with a growth factor which then diffuses out, as indicated by the arrows. In addition, or alternatively, the depot implant could contain a radiopaque marker comprising barium, calcium, or such other suitable material. Such markers can be utilized for tracking purposes and ensuring proper positioning through a radiograph.

As such, the depot implant can be strategically inserted into AVN bone areas in a minimally invasive procedure by entering the body through the skin or through a body cavity or anatomical opening, thus allowing for the smallest damage possible to these structures and correspondingly resulting in less operative trauma for the patient. Preferably, the depot implant is placed in a region of AVN for maximum impact of the growth factor.

The growth factor depot may be constructed from a number of materials comprising natural and synthetic polymers, in solid or gel form, or a combination of each. Examples of plastic materials that the rods could be fabricated from are polyorthoesters (POE), Polylacticglycolic acid (PLGA) Polysaccharides (Saber technology), Polycapralactone, Polyfumarate, Tyrosine polycarbonate, etc. Examples of materials that the gel could be fabricated from are Polyethylene glycol (PEG), Polysaccharides (Saber technology), Polyorthoesters, Hyaluronic acid, Chitosan, Alginate, Albumin, etc.

Figure 4:
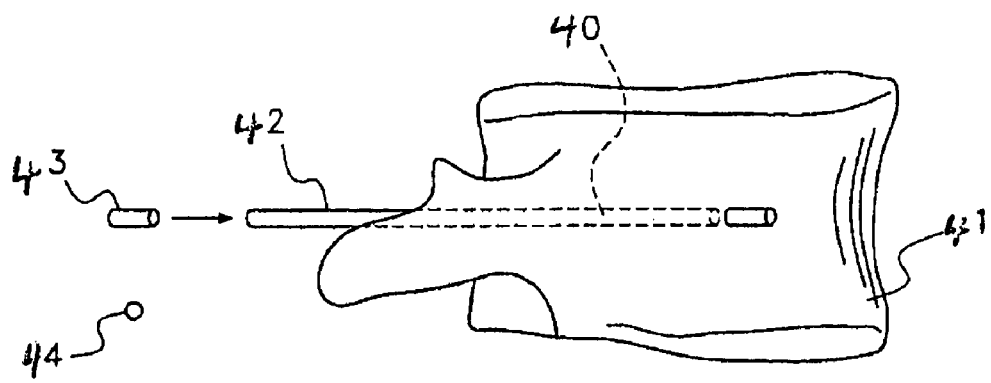
FIG. 4 depicts a perspective view of an embodiment of several growth factor depots in the implanted stage in a vertebral body of the spine.
Figure 5:
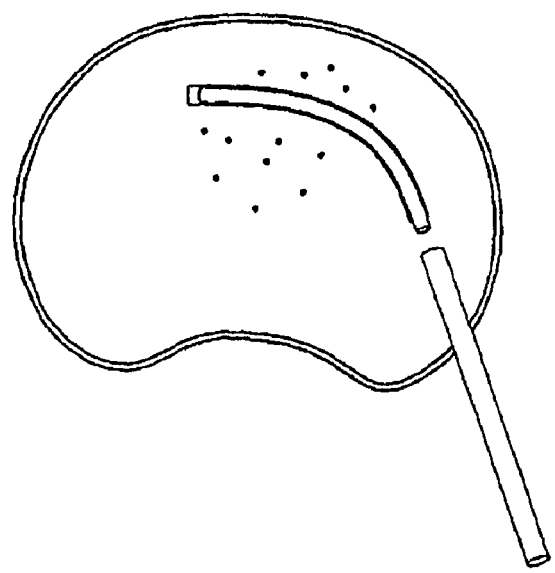
FIG. 5 depicts a top view of an embodiment of the insertion of a growth factor depot implant into a vertebral body of the spine.

Referring now to FIGS. 4 and 5, alternatively either a cylinder (straight or curved rod) or sphere shaped BMP-loaded depot implants and cannula for insertion into a vertebral body is illustrated. In the first step, a bore hole 40 is drilled by a cannula 42 into a vertebral body 41. In an embodiment, such access to the space is gained by a trocar (a sharp pointed needle (not shown)) attached to the cannula 42, allowing for puncture of the body to get into the intended space in the bone. In another embodiment, such access to the space is gained by an orthopedic tool as is well know in the art. Alternatively, or in addition, to the first step, a K-wire, with fluoroscopic imaging, may be used to identify a desired location of the depot implant and then drilling with a canulated drill may be done. In a second step, alternatively either a straight-rod shaped depot implant 43, a sphere-shaped depot implant 44 or a curved rod shaped depot implant as shown in FIG. 5 is then inserted into the vertebral body 41 through the cannula 42. Selection of the type of depot may be based upon a number of factors, including: the shape and/or size of the bone into which the depot is to be implanted; the shape and region of AVN; the percentage of bone density (i.e., the porosity of the remaining bone); and/or the desired speed and distribution of diffusion of the growth factor into the bone; a combination of such factors, etc. Accordingly, as is shown in FIG. 5, a curved depot implant is utilized to match the shape of the vertebral body and thus allow for a more uniform distribution of the growth factor.

Application of the growth factor to the depot may occur at the time of surgery or in any other suitable manner. For example, such application may comprise of dripping or soaking the depot implant in a solution of growth factor. Alternatively (or additionally), the growth factor may be further placed into the internal structure of the depot by placing the depot into a vacuum chamber intra-operatively. Further alternatively (or additionally), the growth factor may be further placed into the internal structure of the depot via insertion of a needle into the center of the depot. It is to be understood, of course, that the internal construction of the depot implant, either solid or hollow, would be independent of the method by which the growth factor may be introduced to the depot implant but may play a role in selection of such method. In many cases, the growth factor may be applied to either the calcium phosphate material or the binding matrix (i.e., collagen) prior to combining the materials and forming into the final depot shape. Indeed, the growth factor can be blended into the natural or synthetic polymer (i.e., POE) and poured into molds of the final shape of the depot implant. Alternatively, the factor, such as a bone morphogenetic protein in a suitable liquid carrier, may be applied onto and/or into the porous load depot body after forming into the final shape by soaking, dripping, etc.

It should be noted, of course, that the BMP load in the depot acts as an osteoinductive and angiogenic factor. Indeed, the preferred angiogenic factors are the recombinant human bone morphogenetic proteins (rhBMPs) because they are available in unlimited supply and do not transmit infectious diseases. Most preferably, the bone morphogenetic protein is a rhBMP-2, rhBMP-4, rhBMP-7, or heterodimers thereof.

Recombinant BMP-2 can be used at a concentration of about 0.4 mg/ml to about 50.0 mg/ml, preferably near 25 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All angiogenic factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

Figure 6:
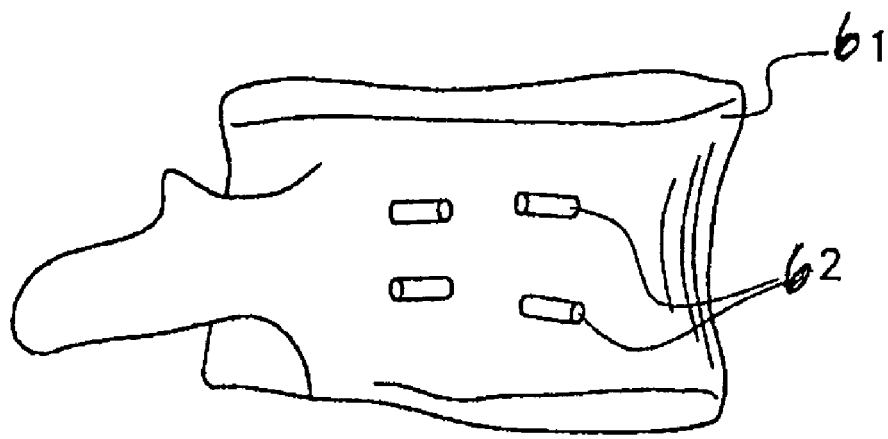
FIG. 6 depicts a perspective view of an embodiment of the insertion of a growth factor depot implant into a vertebral body of the spine.
Figure 7:
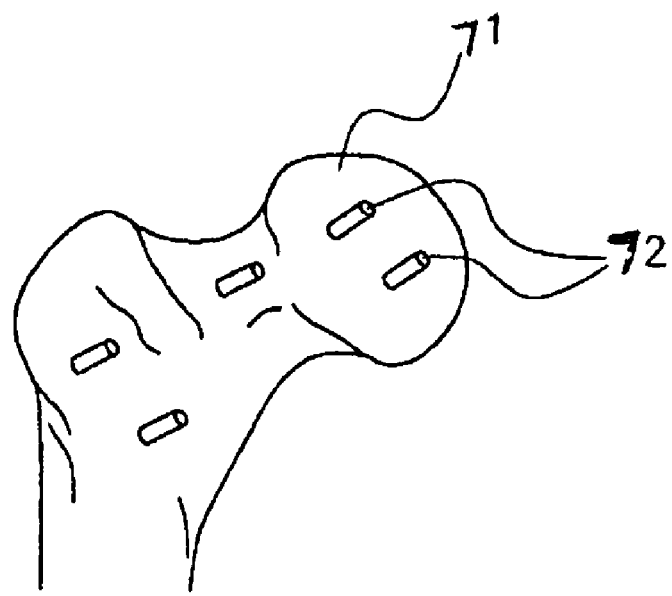
FIG. 7 depicts a perspective view of an embodiment of several growth factor depots in an implanted stage in a femur body of the hip.

Referring now to FIGS. 6 and 7, a vertebral body 61 of the spine and a femur body 71 of the hip are shown implanted with several growth factor depot implants 62 and 72, respectively. The depot implants composition may be comprised of a dense collagen scaffold impregnated with calcium phosphate particles. The scaffold as disclosed herein has a high porosity and an adequate pore size in order to facilitate growth factor seeding and diffusion throughout the whole of the bone structure. Preferably, the scaffold is constructed to be in a range of 2-40% porosity. In addition, the scaffold is biodegradable such that it is absorbed by the surrounding bone tissues without the necessity of a surgical removal. The rate at which degradation occurs is designed to coincide with the optimal release of the growth factor. Furthermore, according to an embodiment of the present invention, a collagen material is used to make up the scaffold as it is tough and inextensible, with great tensile strength, the main component of cartilage, ligaments and tendons, and the main protein component of bone and connective tissue. As mentioned above, selection of the shape and size of the depot implant may be done on the basis of a number of factors.

The dense collagen scaffold is impregnated with calcium phosphate particles. As calcium phosphate is a mineral containing calcium ions (Ca2+) together with orthophosphates (PO43−), metaphosphates or pyrophosphates (P2O74−) and occasionally hydrogen or hydroxide ions, it is easily absorbed by the body as a raw material for new bone cell growth. As angiogenesis or new blood vessel growth occurs the calcium phosphate particles and associated minerals provide the ingredients to support bone regeneration of the previously damaged bone tissue, caused by AVN, or to develop new bone. In a preferred embodiment of the invention, the calcium phosphate is either hydroxyapaptite or tri-calcium phosphate, or a biphasic blend of the two, ideally in a ratio of 15HA/85TCP to 35HA/65TCP.

Accordingly, in this aspect of the invention the density of the depot is much higher than a typical BMP sponge carrier so that the release of the BMP is much slower. As such, the slower time release kinetic properties of this depot avoids the potential for local transient bone resorption, which would aggravate the already depleted cellular constituents of the bone tissue as caused by AVN. This release mechanism permits a continuous stimulation of new blood vessel growth in the AVN region without initial bone tissue resorption that may further weaken the AVN region. In addition, the calcium phosphate component of the depot will also facilitate the prevention of local bone resorption by providing slower release of the BMP due to its increased binding potential and also act as a local source of calcium and phosphate to the cells attempting to deposit new bone as a result of the new blood supply generated by the new vessel growth.

In some embodiments, anti-inflammatory and or antibiotic agents are also incorporated in the depot implant. Both of these categories of agents will enhance the healing process by either eliminating unwanted bacteria or reducing the inflammatory process. Antibiotic agents are well known in the art. Besides the addition of anti-inflammatory agents known in the art, the anti-inflammatory process can also be achieved by cytokine antagonists or cytokine receptor antagonists (competitive or non-competitive cytokine inhibition) to inhibit the inflammatory actions of pro-inflammatory agents such as tumor necrosis factor (TNF), interleukins (IL), and other cytokines. The anti-cytokine agent is adapted to disrupt inflammatory elements at or adjacent to the site of AVN. The anti-cytokine agent may include, for example, a pro-inflammatory receptor antagonist such as an anti-TNF-α agent, which will effectively compete for the TNF-α receptor and inhibit a pro-inflammatory response.

The term "anti-cytokine agent" shall mean any molecule, cell, or physical stimulus which decreases, blocks, inhibits, abrogates or interferes with the pro-inflammatory cascade of cytokine proteins leading to an inflammatory response. For example, a suitable "tumor necrosis factor alpha antagonist" or "TNF-α" antagonist can bind TNF, and includes anti-TNF antibodies and/or receptor molecules which bind specifically to TNF. A suitable TNF antagonist can also prevent or inhibit TNF synthesis and/or TNF release and includes compounds such as thalidomide, tenidap, and phosphodiesterase inhibitors, such as, but not limited to, pentoxifylline and rolipram.

Interleukin-1 is a pro-inflammatory cytokine similar in action to TNF-α. For example, certain inhibitors of this protein are similar to those developed to inhibit TNF-α. One such example is Kineret® (anakinra) which is a recombinant, non-glycosylated form of the human interleukin-1 receptor antagonist (IL-1Ra). Another suitable anti-cytokine agent is AMG 108, which is a monoclonal antibody that blocks the action of IL-1.

Still other anti-cytokine agents include but are not intended to be limited to NF Kappa B inhibitors such as for example glucocorticoids such as fluocinolone, nonsteroidal anti-inflammatory drugs (NSAIDs), such as sulindac and tepoxalin, antioxidants, such as dithiocarbamate, and other compounds such as sulfasalazine [2-hydroxy-5-[-4-[C2-pyridinylamino) sulfonyl]azo]benzoic acid], clonidine and autologous blood-derived products, such as Orthokine.

In other embodiments, the angiogenic compositions used in this invention further comprise a therapeutically effective amount to stimulate or induce blood vessel growth of substantially pure pluripotent mesenchymal stem cells or growth factor or protein in a pharmaceutically acceptable carrier. The choice of carrier material for the angiogenic composition is based on biocompatibility, biodegradability, mechanical properties and interface properties. The particular application of the compositions of the invention will define the appropriate formulation. Potential carriers include calcium phosphates, collagen, hyaluronic acid, polyorthoesters, polylactic acids, poly glycolic acids, PLGA copolymers, polyanhydrides, polymeric acrylic esters, calcium sulphates and demineralized bone. The carrier may be any suitable carrier capable of delivering the proteins, nucleotide sequences, or the like. Most preferably, the carrier is capable of being eventually resorbed into the body. One preferred carrier is an absorbable collagen sponge marketed by Integra Life-Sciences Corporation under the trade name Helistat® Absorbable Collagen Hemostatic Agent. Another preferred carrier is a biphasic calcium phosphate ceramic. Ceramic blocks and granules are commercially available from Sofamor Danek Group, Deggendorf, Germany.

All publications cited in the specification, both patent publications and non-patent publications, are indicative of the level of skill of those skilled in the art to which this invention pertains. All these publications, including application Ser. No. 11/418,947, are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A method for treating avascular necrosis of bone comprising:
    a) identifying a target site with an avascular necrosis area of bone; and
    b) administering to the site a therapeutic agent comprising an angiogenic substance comprising a growth factor, wherein the therapeutic agent is administered in a depot implant comprising a dense scaffold having a porosity of 2% to 40% and containing collagen and impregnated with calcium phosphate particles, the dense scaffold disposed throughout the entire depot implant and having adequate pore size and porosity to facilitate seeding and diffusion of the growth factor to slow its release from the depot implant to host bone, wherein the growth factor is in liquid form and completely fills a central hollow chamber of the depot implant.

2. The method according to claim 1, wherein the therapeutic agent further comprises an anti-inflammatory agent.

3. The method according to claim 2, wherein the anti-inflammatory agent comprises anti-cytokine agents selected from the group consisting of TNF-α inhibitors, IL-1 inhibitors, IL-6 inhibitors, IL-8 inhibitors, IL-12 inhibitors, IL-15 inhibitors, IL-10, NFkappaB inhibitors, and IFN-γ.

4. The method according to claim 1, wherein the therapeutic agent further comprises an antibiotic agent.

5. The method according to claim 1, wherein the growth factor is at least one of: BMP-2, rhBMP-2, BMP-4, rhBMP-4, BMP-6, rhBMP-6, BMP-7(OP-1), rhBMP-7, GDF-5, rhGDF-5, LIM mineralization protein, platelet derived growth factor (PDGF), transforming growth factor-β(TGF-β), insulin-related growth factor-I (IGF-I), insulin-related growth factor-II (IGF-II), fibroblast growth factor (FGF), beta-2-microglobulin (BDGF II), parathyroid hormone (PTH), PGE2 agonist, granulocyte colony stimulating factor (G-CSF), vascular endothelial growth factor (VEGF), and matrix metalloproteinase (MMP).

6. The method according to claim 1, wherein the depot implant is biodegradable.

7. The method according to claim 1, wherein the depot implant allows for implantation and retention into the target site of the therapeutic agent.

8. The method according to claim 1, wherein the dense scaffold is constructed from a gel.

9. The method according to claim 1, wherein the depot implant comprises polylactic acid, polygylcolic acid, or polylacticglycolic acid (PLGA).

10. The method according to claim 1, wherein the depot implant has a physical structure generally in the shape of one of a cylinder or a sphere.

11. The method according to claim 10, wherein the cylinder shape is 5 to 20 mm in length.

12. The method according to claim 10, wherein the cylinder shape is 1 to 5 mm in diameter.

13. The method according to claim 10, wherein the cylinder shape is either straight or curved.

14. The method according to claim 1, wherein administering the therapeutic agent comprises utilizing a cannula or large bore needle to inject the depot into the target site.

* * * * *